(12) United States Patent
McGuckin et al.

(10) Patent No.: US 6,425,887 B1
(45) Date of Patent: Jul. 30, 2002

(54) MULTI-DIRECTIONAL NEEDLE MEDICAL DEVICE

(75) Inventors: James Frederick McGuckin, Radnor, PA (US); Edward J. Morris, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 77 days.

(21) Appl. No.: 09/668,067

(22) Filed: Sep. 22, 2000

Related U.S. Application Data (62) Division of application No. 09/457,844, filed on Dec. 9, 1999.
(60) Provisional application No. 60/130,597, filed on Apr. 22, 1999, and provisional application No. 60/111,624, filed on Dec. 9, 1998.

(51) Int. Cl.[7] ................................................ A61M 5/32
(52) U.S. Cl. ...................................................... 604/272
(58) Field of Search ............................... 604/272, 204, 604/117, 273, 274, 93.01

(56) References Cited

U.S. PATENT DOCUMENTS

| | | | |
|---|---|---|---|
| 4,013,080 A | | 3/1977 | Froning |
| 4,343,306 A | * | 8/1982 | Mericle ..................... 604/218 |
| 4,403,617 A | | 9/1983 | Tretinyak |
| 4,518,383 A | | 5/1985 | Evans |
| 4,616,656 A | | 10/1986 | Nicholson et al. |
| 4,799,495 A | * | 1/1989 | Hawkins et al. ............. 600/567 |
| 4,926,860 A | | 5/1990 | Stice et al. |
| 4,958,901 A | | 9/1990 | Coombs |
| 4,969,888 A | | 11/1990 | Scholten et al. |
| 5,031,634 A | | 7/1991 | Simon |
| 5,067,957 A | | 11/1991 | Jervis |
| 5,098,400 A | * | 3/1992 | Crouse et al. ............... 604/192 |
| 5,108,404 A | | 4/1992 | Scholten et al. |
| 5,219,358 A | | 6/1993 | Bendel et al. |

(List continued on next page.)

FOREIGN PATENT DOCUMENTS

| | | |
|---|---|---|
| EP | 0550258 | 7/1993 |
| EP | 0769272 | 4/1997 |
| WO | 9627328 | 9/1996 |

OTHER PUBLICATIONS

G.R. Zadno and T.W. Duerig: Linear Superelasticity in Cold–Worked NI–TI; Engineering Aspects of Shape Memory Alloys, pp. 414–419.

Allan Siperstein, M.D. et al., Liver Tumor Ablation Program: University of California, San Francisco / Mount Zion Medical Center.

Website printout—http://www.daum.de/mri/softtissue/smartguide.html; "SmartGuide™ CT/MRI"; (date unknown); two pages; Daum Corp., Chicago, IL.

U.S. application No. 09/377,293 filed Aug. 19, 1999 (Abstract and Drawings Only).

*Primary Examiner*—Joseph Pelham
*Assistant Examiner*—Daniel Robinson
(74) *Attorney, Agent, or Firm*—Richard J. Godlewski (57) ABSTRACT

A needle assembly (70) comprising an infusion needle (11) that includes a plurality of needle cannulae (13) made of a superelastic material such as nitinol. The needle cannulae are cold-worked or heat annealed to produce preformed bends (16) that can be straightened with in passageway (21) of a coaxial outer cannula (12) for introduction into the body of a patient. Upon deployment from the outer cannula, the needle cannulae substantially return to their preformed configurations for the introduction or extraction of materials at areas lateral to the entry path of the needle assembly. The plurality of needle cannulae (13) can be variably arranged or configured for their distal tip portions to attain a desired infusion pattern such as an umbrella shaped array (75), and/or be staggered axially.

23 Claims, 11 Drawing Sheets

U.S. PATENT DOCUMENTS

| | | | |
|---|---|---|---|
| 5,221,269 A | * 6/1993 | Miller et al. | 604/170.03 |
| 5,231,989 A | 8/1993 | Middleman et al. | |
| 5,238,004 A | 8/1993 | Sahatjian et al. | |
| 5,242,448 A | 9/1993 | Pettine et al. | |
| 5,243,996 A | 9/1993 | Hall | |
| 5,295,493 A | 3/1994 | Radisch, Jr. | |
| 5,345,937 A | 9/1994 | Middleman et al. | |
| 5,354,279 A | 10/1994 | Höfling | |
| 5,464,395 A | * 11/1995 | Faxon et al. | 604/103.02 |
| 5,533,982 A | 7/1996 | Rizk et al. | |
| 5,542,434 A | 8/1996 | Imran et al. | |
| 5,556,410 A | 9/1996 | Mittermeir et al. | |
| 5,573,542 A | 11/1996 | Stevens | |
| 5,597,378 A | 1/1997 | Jervis | |
| 5,601,572 A | 2/1997 | Middleman et al. | |
| 5,607,389 A | 3/1997 | Edwards et al. | |
| 5,628,734 A | 5/1997 | Hatfalvi | |
| 5,636,641 A | 6/1997 | Fariabi | |
| 5,741,278 A | 4/1998 | Stevens | |
| 5,766,218 A | * 6/1998 | Arnott | 24/16 PB |
| 5,853,423 A | 12/1998 | McGregor et al. | |
| 5,895,395 A | 4/1999 | Yeung | |
| 6,143,004 A | * 11/2000 | Davis et al. | 606/144 |
| 6,190,353 B1 | * 2/2001 | Makower et al. | 600/137 |
| 6,217,554 B1 | 4/2001 | Green | |

\* cited by examiner

MULTI-DIRECTIONAL NEEDLE MEDICAL DEVICE

CROSS-REFERENCE TO RELATED APPLICATION

This is a Divisional application of U.S. patent application Ser. No. 09/457,844 filed Dec. 9, 1999, which application claims the benefit of U.S. Provisional Patent Applications Serial No. 60/111,624 filed Dec. 9, 1998 and Serial No. 60/130,597 filed Apr. 22, 1999.

TECHNICAL FIELD

This invention relates generally to medical devices and more particularly, to needles that are curved for indirect infusion access within the body.

BACKGROUND OF THE INVENTION

Medical procedures involving the vertebrae are typically complicated because of the preciseness required to avoid both neural damage and injury to major blood vessels, as well as the indirect path that is usually required to access the treatment site. This is certainly the case when performing a vertebroplasty, a procedure whereby bone cement, most commonly methyl methacrylate, is injected into a vertebral body to provide stabilization and/or pain relief in selected patients having a spinal condition such as osteolytic metastasis and myeloma, painful or aggressive hemangioma (benign lesions of the spine), or painful osteoporotic vertebral collapse. Standard treatment practice depends on the region of the spine being treated. For the cervical vertebrae, anterolateral access is used with a 15 gauge needle. The large vessels adjacent to the vertebra are laterally manipulated by the radiologist to provide an access site between the vessels and the pharyngolarynx. An upward access route is required because the needle must be introduced below the mandible. When accessing the thoracic or lumbar vertebrae, typically a large 10 gauge needle is used following a transpedicular or posterolateral approach. The transpedicular route is preferred to avoid spinal nerve injury and to decrease the probability of the cement leaking out into tissues adjacent to the vertebral body. To obtain a complete filling of a damaged vertebral body, it is often required that a second transpedicular access be made from the opposite side. A single infusion usually cannot fill the entire target area because the needle tip cannot be redirected from the original plane of entry. Continued infusion of cement from the first access site will usually not result in an adequate infusion due to the tendency of the material to set before it fills all of the affected area, thereby becoming a barrier to itself. Furthermore, the thick density of the marrow and structures, such as veins, usually acts to impede free flow of the cement within the vertebral body. Another concern during the procedure is accidental puncture of the these veins. Because vertebral veins lead directly to the lungs, there is a significant risk of pulmonary embolism if cement is accidentally introduced therein.

The inability to adequately maneuver the needle cannula tip within a body or around structures is a major limitation of the straight needle. Additional needle sticks to complete a medical procedure provide discomfort to the patient and additional risk of leakage and other complications. In order to sufficiently access a vertebral body for complete infusion of cement, the tip must be able to be deflected at significantly large angles from the original axis. This would require that the needle have a distal bend so that it could be rotated to selectively direct the material. Rigid curved needles are well known for suturing applications; however, adding anything more than a slight bend to an infusion needle limits its access path and ability to deeply penetrate tissue, especially bone. For example, a rigid curved needle would be unsuitable for use in a vertebroplasty procedure where the needle cannula must be driven through the bone and deep into the vertebral body using a relatively straight approach and maintained in place to avoid additional damage to the entry site. While the initial access must be done with a straight needle of sufficient strength to penetrate bone, the ideal approach would be to be able to direct a lateral infusion of cement following penetration, and then to withdraw the needle along its original path. Accomplishing this is problematic in that the density and resistance of the tissue at the treatment site can require that the inner infusion member be nearly as stiff as the outer piercing cannula. A certain degree of rigidity is required to be able to maneuver the inner member and accurately direct the flow of material. While stainless steel infusion needles having a slight distal bend are known, the amount of curvature necessary to provide adequate lateral infusion would not be possible in that the needle would be plastically deformed once inside the outer restraining cannula and be unable to resiliently return to its preformed shape. Thus, a second needle access would still be required to provide adequate filling.

Other medical procedures provide similar problems when a single straight needle is used. One example is tumor ablation where percutaneous ethanol injection is used to treat carcinoma of the liver and kidney. Originally introduced as a palliative treatment for inoperable hepatocellular carcinoma of the liver, ethanol injection has now been shown to have curative potential comparable to resection in many patients, especially for smaller tumors. Current practice has been to directly inject ethanol into masses using a straight needle and allow the ethanol to infuse from one or more side holes into the tissue. The problem is that the infusion may not penetrate any deeper than the needle tract and thus, portions of the tumor are not effectively treated. It is desired to provide a device for more effective infusion of ethanol into the tumor mass.

SUMMARY OF THE INVENTION

The foregoing problems are also solved and a technical advance is achieved in a medical needle device for use for example for infusion or aspiration, and made of a rigid superelastic material and having at least one preformed bend along the distal portion of its length. The needle is used coaxially with a second hollow cannula for restraining the needle in a substantially straight orientation during percutaneous introduction to the target site, whereby the needle is deployed to resiliently return to its preformed configuration. The ability of the preformed needle to deflect laterally upon exiting the restraining cannula allows it to infuse or aspirate material at multiple points within different planes in the body by rotating the needle about its longitudinal axis. This is important in helping to reduce or eliminate the need for additional "sticks" with the restraining cannula. It also allows the operator to make an entry from one direction, then to deploy the curved to reach a site that cannot be accessed directly, such as where another structure lies along the access path, thereby blocking the target site.

The preferred material for the needle device is a superelastic, shape memory alloy such as nitinol (Ni—Ti); however, there are other non Ni—Ti alloys that may be used. A nitinol alloy is selected that has properties whereby the temperature at which the martensitic to austenitic phase change occurs is lower than the working temperature of the device (i.e., room temperature). As described by Jervis in U.S. Pat. No. 5,597,378 filed Oct. 2, 1992 and incorporated herein by reference, a permanent bend may be heat set in a superelastic nitinol cannula by maintaining the cannula in the desired final shape while subjecting it to a prescribed high temperature for a specific time period. The cannula can be elastically manipulated far beyond the point at which stainless steel or other metals would experience plastic deformation. Nitinol and other superelastic materials, when sufficiently deformed, undergo a local phase change at the point of stress to what is called "stress-induced martensite" (SIM). When the stress is released, the material resiliently returns to the austenitic state.

A second method of imparting a permanent bend to the material is by a process commonly known as cold working. Cold working involves mechanically overstressing or overbending the superelastic cannula. The material within the bending region undergoes a localized phase shift from austenite to martensite and does not fully return to its original shape. In the case of the cold-worked cannula, the result is a permanent curve about the bending zone which has been locked in to at least a partial martensitic crystalline state. In contrast, the entire heat-annealed cannula is in a austenitic condition, even in the curved region, and only is temporarily transformed to martensite under sufficient bending stresses. Therefore, the flexural properties of the annealed cannula vary little across its length. Conversely, the bend of cold-worked cannula, which contains martensite, has increased resistance to deformation and therefore, holds its shape better than the more flexible bend of the pure austenitic cannula. This increased rigidity can be an advantage for certain clinical applications.

In a first embodiment of the invention suitable for many clinical applications involving infusion an introducer trocar or stylet are used with either a restraining cannula or needle cannula therewithin depending on the luminal size of the needle, to facilitate access of tissue and/or prevent coring tissue into the distal tip of the device. The infusion needle cannula is introduced through the outer restraining cannula after access has been established and the trocar or stylet is removed. Depending on the size of the cannulae, the degree of the preformed bend, or the method used to form the bend, the inner cannula may slightly deform the outer cannula as the preformed bend is constrained within the outer cannula. As a result, the outer cannula may be deflected a few degrees from its normal longitudinal axis at a point corresponding to the bend of the inner cannula. As the inner cannula is deployed from the outer cannula, it deflects laterally until the entire region of the bend is unsheathed. In the preferred embodiments the distal opening of the inner cannula is oriented at a large angle (preferably within the range of 60–90°) from the original longitudinal axis when the inner needle is fully deployed.

The ability of the inner cannula to deflect at a significant angle from the original longitudinal axis has great utility in a number of applications where straight access is required followed by redirection of the distal opening. This permits access to a different site without the necessity of withdrawing and reintroducing the needle. A primary example of such a procedure is vertebroplasty in which infusion of the stabilizing cement with a conventional straight needle often requires a second stick to provide a complete filling to stabilize the vertebral body while avoiding damage to delicate structures such as veins. As with the standard single-needle procedure involving the thoracic or lumbar regions of the spine, a transpedicular approach is normally used whereby the larger outer needle cannula, such as a coaxial Jamshidi-type needle, is introduced into the damaged or diseased vertebral body. The outer needle includes an inner introducer trocar which is then replaced with a inner curved needle for infusion of the cement. The ability of the curved needle to self-deflect laterally and be rotated to reach multiple planes, gives it a significant advantages over straight needles which have a limited range of infusion. Because of this additional range of movement, the curved needle of the present invention can usually complete the vertebroplasty procedure with a single access or "stick" of the vertebral body. This avoids additional discomfort and risks to the patient, which include complications from leakage of cement or inadvertent infusion into non-target areas.

In addition to using the coaxial needle for infusion of cement in the above embodiment, the device can also be adapted for aspirating material or serving as a conduit for the introduction of other devices. It is contemplated that the present invention can be used for a percutaneous corpectomy, a procedure which involves fusion and decompression of two or more vertebrae by first aspirating tissue from the damaged vertebral bodies, then introducing a carbon fiber composite cage packed with bone graft material to serve as scaffolding for the affected vertebrae. Once the cage is properly positioned, methyl methacrylate or another suitable material is infused into the vertebral bodies to secure the prosthesis. The percutaneous corpectomy offers less trauma and with the reinforcement cage, provides superior rigidity over a conventional corpectomy utilizing bone graft material alone.

In another aspect of the invention, the coaxial needle can be adapted for paraspinal use to inject medicaments within the neural canal or epidural space as part as management and/or diagnosis of pain. Preferably, the outer cannula has a tip adapted for piercing soft tissue. This outer needle cannula, preferably about 21 gauge, is introduced percutaneously parallel to the spinal column along with an internal stylet with matched bevel to prevent the coring of tissue into the distal opening. The stylet is removed and the curved needle, about 25 gauge, is inserted into the outer cannula. The needle assembly is then maneuvered to contact a nerve root during a diagnostic procedure to help recreate pain symptoms of the patient. The inner infusion needle also includes a stylet which is situated within the passageway of the needle as it is directed to the target site. The stylet is then removed from the infusion needle and medicaments, commonly steroids such as Celestone (injected with lidocaine), Kenalog, or methylprednisone are introduced to the treatment site. The inner needle is then withdrawn into the outer sheath cannula and both are withdrawn from the patient.

Another use of the smaller gauge paraspinal needle is for diskography procedure. Diskography consists of injecting a contrast agent (preferably nonionic contrast media) directly into the disk to delineate the extent of any malformations or injury to the vertebral body.

Yet another embodiment of the invention solves the problem of infusion of ethanol into a tumor mass by utilizing a plurality of curved needle cannulae that can be deployed within an introducer cannula into the tumor where they radiate outward into an umbrella-shaped configuration. Therefore, infusion can take place at multiple points within the tumor to provide wider dispersion of the ethanol. Following treatment, the needle cannulae are withdrawn into the cannula and the device is removed from the patient.

In a related embodiment, one or more needle cannulae are located proximal to the distal end of the infusion needle. These proximally-located cannulae allow infusion of medicaments at different points along the length of the device. By having multiple sets of needles arranged in the umbrella configuration, the volume of tissue treated is increased. The coaxial outer cannula includes a plurality of side apertures that allow the proximally-located needle cannulae to deploy after the infusion needle is placed at the desired location in the body and the outer cannula is withdrawn. An outer sheath over the coaxial outer cannula selectively exposes the side apertures to permit the appropriate alignment of needle cannulae and apertures when there are multiple rows of each.

The value of the present invention includes any clinical situation where a straight approach is dictated and there is a need to avoid an obstructing structure in the entry path(a large vessel, bowel loop, etc.) or to redirect to a more lateral pathway to infuse medicaments or to aspirate, such as to drain an abscess. In addition to infusion or aspiration, the present invention can function as a conduit for introducing and/or directing the path of other medical devices within the body such as radio-frequency ablation catheters or wire guides. This invention would allow a straight approach to a critical juncture whereafter the curved needle can be deployed to precisely direct the device to the desired anatomical site, especially in situations such as a luminal bifurcation or when access to an ostium is required. Another use of the present invention is to place the needle in a scope such a bronchoscope or colonoscope which can serve as the outer constraining device. Under visualization, the inner needle then can be directed to perform a biopsy or other type of procedure. Embodiments of the present invention will now be described by way of example with reference to the accompanying drawings.

DETAILED DESCRIPTION

Figure 1:
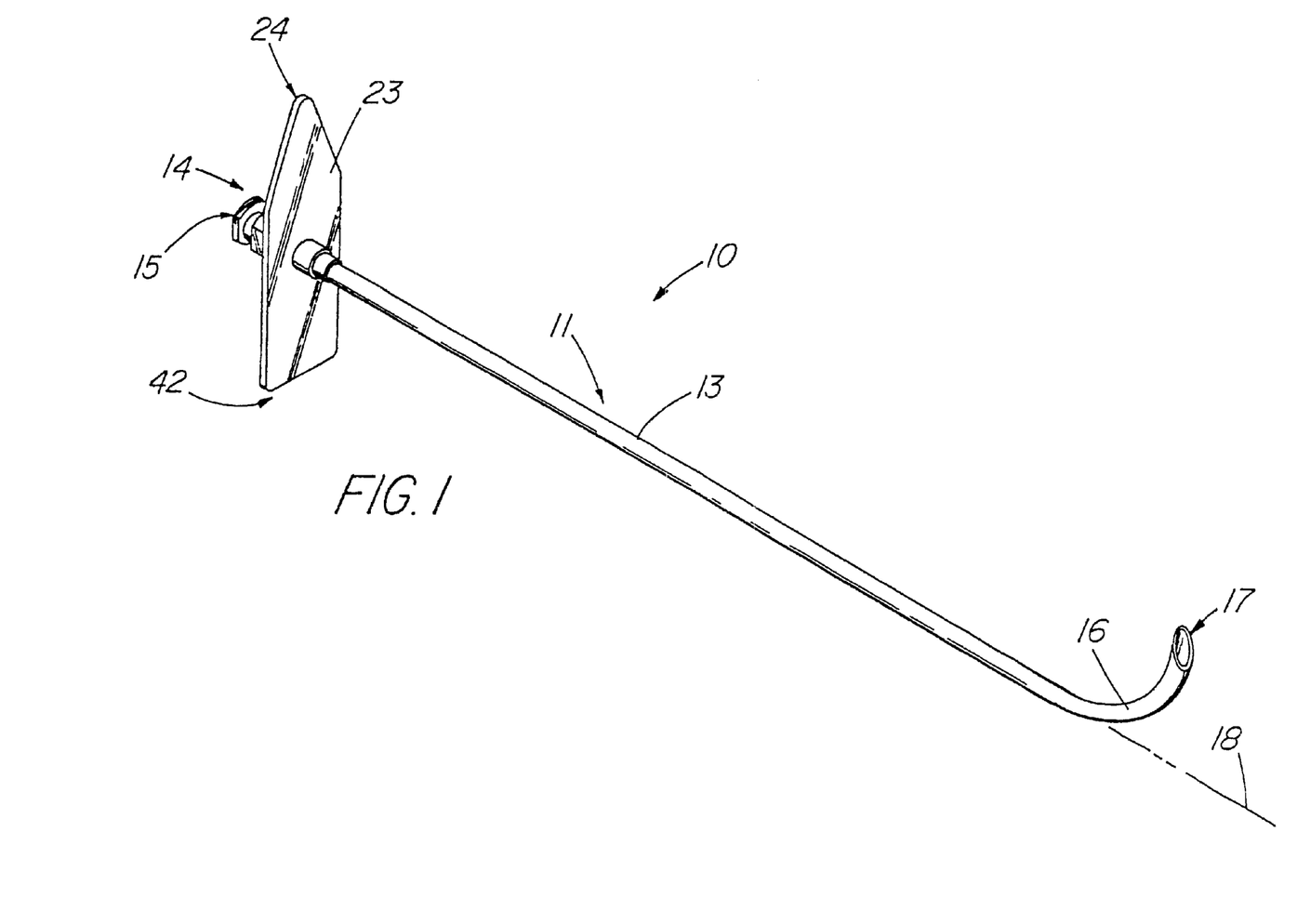
FIG. 1 depicts a pictorial view of an illustrative embodiment of the curved needle cannula.

FIG. 1 depicts a pictorial view of an illustrative embodiment of the needle assembly 10 comprising a medical needle 11 with a preformed bend 16 for lateral infusion of medicaments and other materials, or for aspiration. As defined herein, the needle assembly 10 can comprise the needle 11 alone or the needle 11 in combination with other components that are part of this disclosure. The needle 11 as defined herein, comprises one or more needle cannulae having a preformed bend 16. The needle 11 of FIG. 1 is comprised of a superelastic alloy needle cannula 13, preferably nitinol, that is soldered or otherwise affixed to a well-known needle hub 14 using one of selected well-known techniques, including that of Hall described in U.S. Pat. No. 5,354,623 whose disclosure is expressly incorporated herein by reference, and a flange 23 which has a first tapered or pointed end 24 whose shape is readily distinguishable from the second, squared end 42. The first end 24 corresponds to the direction of the preformed bend 16 formed in needle cannula 13 of the needle 11. The bend is formed in the nitinol needle cannula 13 by either the well-known process of deforming the cannula under extreme heat for a prescribed period of time, which produces a cannula entirely in the austenitic state, or by cold working the cannula, which involves applying a large amount of mechanical stress to deflect the cannula well beyond the desired amount of permanent bend. Cold working permanently locks a portion of crystalline structure of the bending zone into at least a partial martensitic condition while the unstressed portions of the cannula remains in the austenitic state. Cold worked Ni—Ti alloys are discussed in "Linear Superelasticity in Cold-Worked Ni—Ti", (Zadno and Duerig) pp. 414 to 419, in *Engineering Aspects of Shape Memory Alloys*, Butterworth-Heineman, Boston, Mass. (Duerig et al, editors) which is incorporated herein by reference. In addition to nitinol, superelastic or pseudoelastic copper alloys, such as Cu—Al—Ni, Cu—Al—Zi, and Cu—Zi are available as alternative needle cannula materials. Flexible polymeric materials with sufficient rigidity for both deployment and shape memory to assume a desired curve may also be used in certain applications, either alone or in combination with reinforcing metal components, such as a metal braid or tip.

The preformed bend 16 of the needle 11 of the present invention comprises the distal portion of the needle cannula 13, preferably close to about 25% of the needle cannula 13 length in the embodiment of FIG. 1. Because of the larger size of the needle, preferably 10–18 gauge, this particular embodiment is suitable for penetrating a vertebral body to perform a vertebroplasty or percutaneous corpectomy procedure. A more preferred range would be 12–17 gauge, with the most preferred cannula size being 13–15 gauge. With regard to a vertebroplasty and corpectomy procedures, the larger gauge cannula has both the strength to penetrate dense bone material, as well as a sufficient lumen diameter to aspirate material from the vertebral body as well as infuse highly viscous bone cement, such as methyl methacrylate. The preferred preformed bend 16 of the needle 11 would have a constant diameter radius. For the embodiment of FIG. 1, the preferred radius of the distal bend is approximately 3.0 cm for a 13 gauge needle, and approximately 2.5 cm for a 14 gauge needle. Although the illustrative embodiment has a constant diameter bend radius, an increasing or decreasing radius bend could be employed for certain clinical applications. Furthermore, it is possible to introduce more than one bend into the superelastic cannula for applications requiring a special needle configuration.

Figure 2:
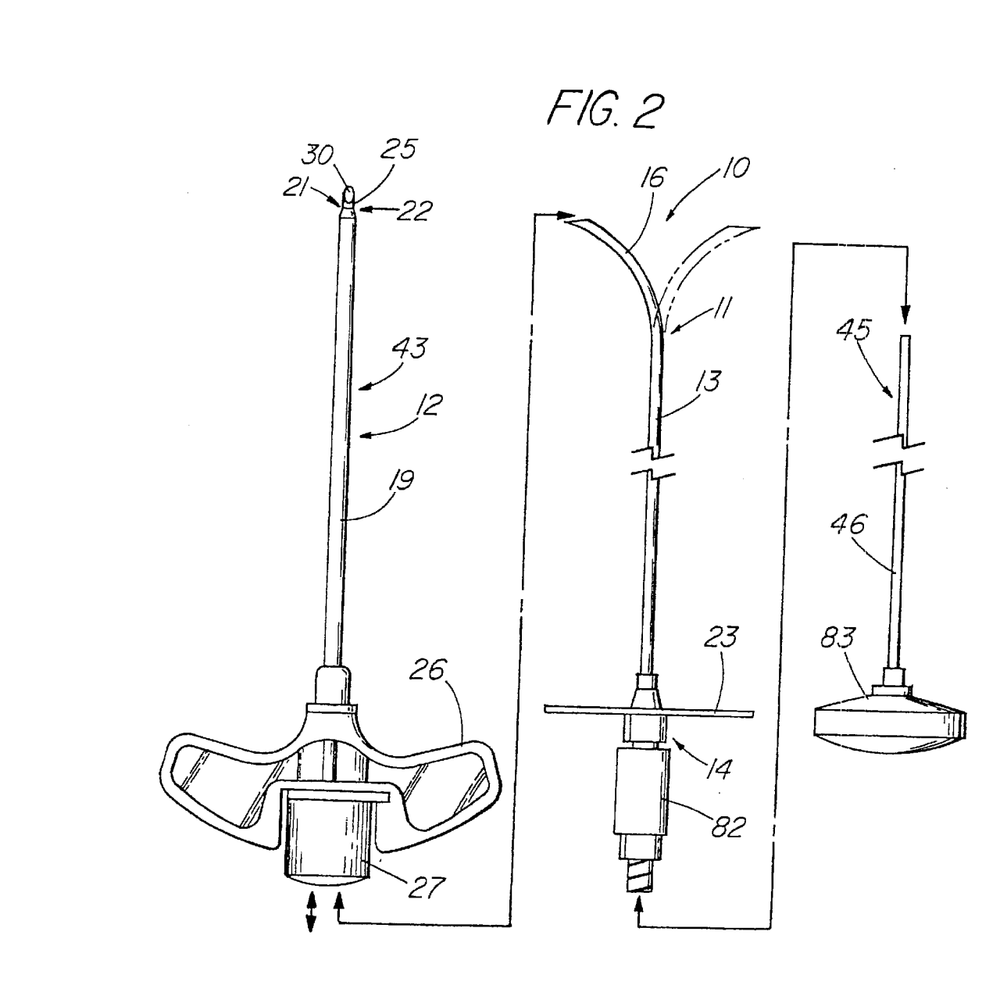
FIG. 2 depicts top views of the outer needle cannula with introducer trocar and the inner curved needle cannula.

The primary purpose of using a nitinol or other superelastic alloy cannula is that it can be constrained into one shape during its passage to the treatment site, then deployed into its preformed configuration without experiencing any plastic deformation. FIG. 2 depicts a pair of needles to be used coaxially in that manner, including the needle 11 of FIG. 1 and a coaxial outer cannula 12 for maintaining the inner needle 11 in a substantially straight configuration while it is being introduced to the treatment site. The embodiment depicted in FIG. 2 is Jamshidi-type needle (Manan Inc., Northbrook), a two-part needle assembly 43, and is most commonly used for accessing dense, hard tissue such as bone, fibrous material, etc. Thus, it is well suited for penetrating the wall of a vertebral body wherein the needle 11 can be deployed. The outer needle assembly 43 of this particular embodiment is comprised of a coaxial outer cannula 12 which includes a stainless steel cannula 19 with an inner passageway 21 that is sufficiently large to accommodate the inner needle 11. For example, the standard 11 gauge Jamshidi-type needle suitable for accessing a vertebral body would be used with 13 gauge inner curved needle. Stainless steel cannula 19 is affixed proximally to a handle 26 and a connector hub 31 (shown in FIG. 3). The connector hub 31 receives the second part of the two-part needle assembly 43, the coaxial outer cannula introducer 52 which in this embodiment, comprises a trocar 25. The trocar hub 27 locks into the handle 26 of the coaxial outer cannula 12. The beveled tip 30 of the trocar 25 extends approximately 5 mm beyond the distal tip 22 of the coaxial outer cannula 12 and assists in penetration. The trocar 25 also serves to prevent the coaxial outer cannula 12 from coring a sample of bone or other material during access.

Figure 3:
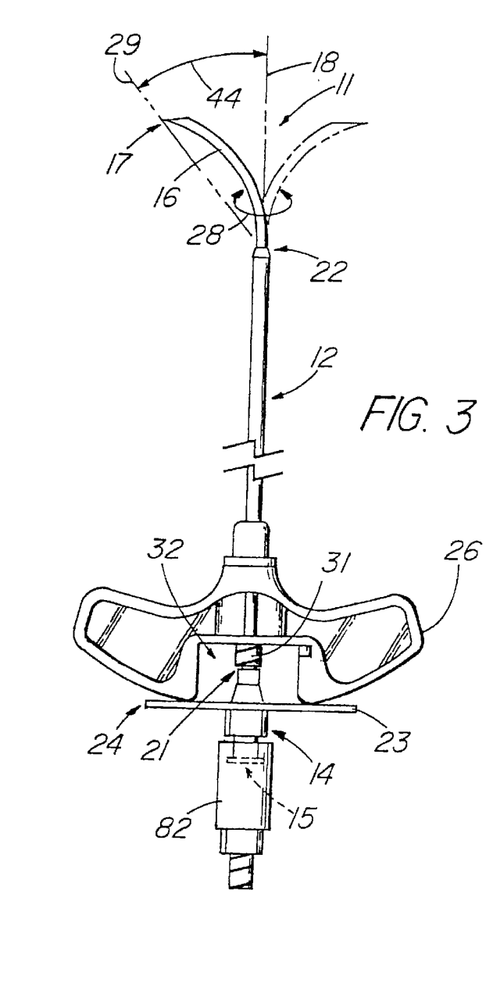
FIG. 3 depicts a top view of the inner curved needle cannula inside the outer needle cannula.

After the outer needle assembly 43 has been directed to the target site, the trocar 25 is removed from the coaxial outer cannula 12 and the needle 11 is inserted into passageway 21 of the coaxial outer cannula 12, as shown in FIG. 3. To maintain patency of the needle passageway 15 and prevent tissue coring during deployment, an inner needle introducer stylet 45 can be introduced coaxially inside the needle. In the illustrative embodiment, the inner needle introducer stylet 45 includes a handle 83 and a shaft 46 which is made of a flexible, high-tensile polymeric material such as polyetheretherketone (PEEK) to allow the stylet 45 to assume the contour of the preformed bend 16 after deployment. The inner needle 11 straightens as it is loaded into the coaxial outer cannula 12. As the region including the preformed bend 16 of the needle 11 extends out from the tip 22 coaxial outer cannula 12 as depicted, it assumes its preformed shape due to the superelastic properties of the needle cannula 13. For infusion, the inner needle introducer stylet 52, which helps prevent coring tissue into the passageway 21 of the coaxial outer cannula 12, is removed. The tapered or "arrow" end 24 of the flange 23 of proximal hub 14 corresponds with the deflection plane 29 of the needle 11. By maneuvering the flange 23, the inner curved needle can be rotated in either direction 28 to reorient the plane of deflection 29 and place the tip opening 17 at multiple locations within the area being treated. In the illustrative embodiment, the opening of the tip 17 is deflected at an angle 44 of approximately 60° to 70° from the longitudinal axis 18 of the device. This gives an illustrative embodiment with a 13 gauge needle 11, a lateral reach, measured from tip 17 longitudinal axis 18, of nearly 30 mm in any direction. While the degree of deflection 44 required is determined by the application and desired lateral reach of the device, it is also limited by the size of the cannula if the permanent bend is to be cold worked into the material. Cold working provides a stiffer bend that can be advantageous in certain applications, such a vertebroplasty and biopsy of dense tissue; however, it is more difficult to permanently deform a larger gauge nitinol cannula without application of extreme heat. For the embodiments contemplated for the present invention, the angle of deflection 44 can encompass a range of 30 to 110°, with a more preferred range of 40 to 90° for most applications.

Figure 4:
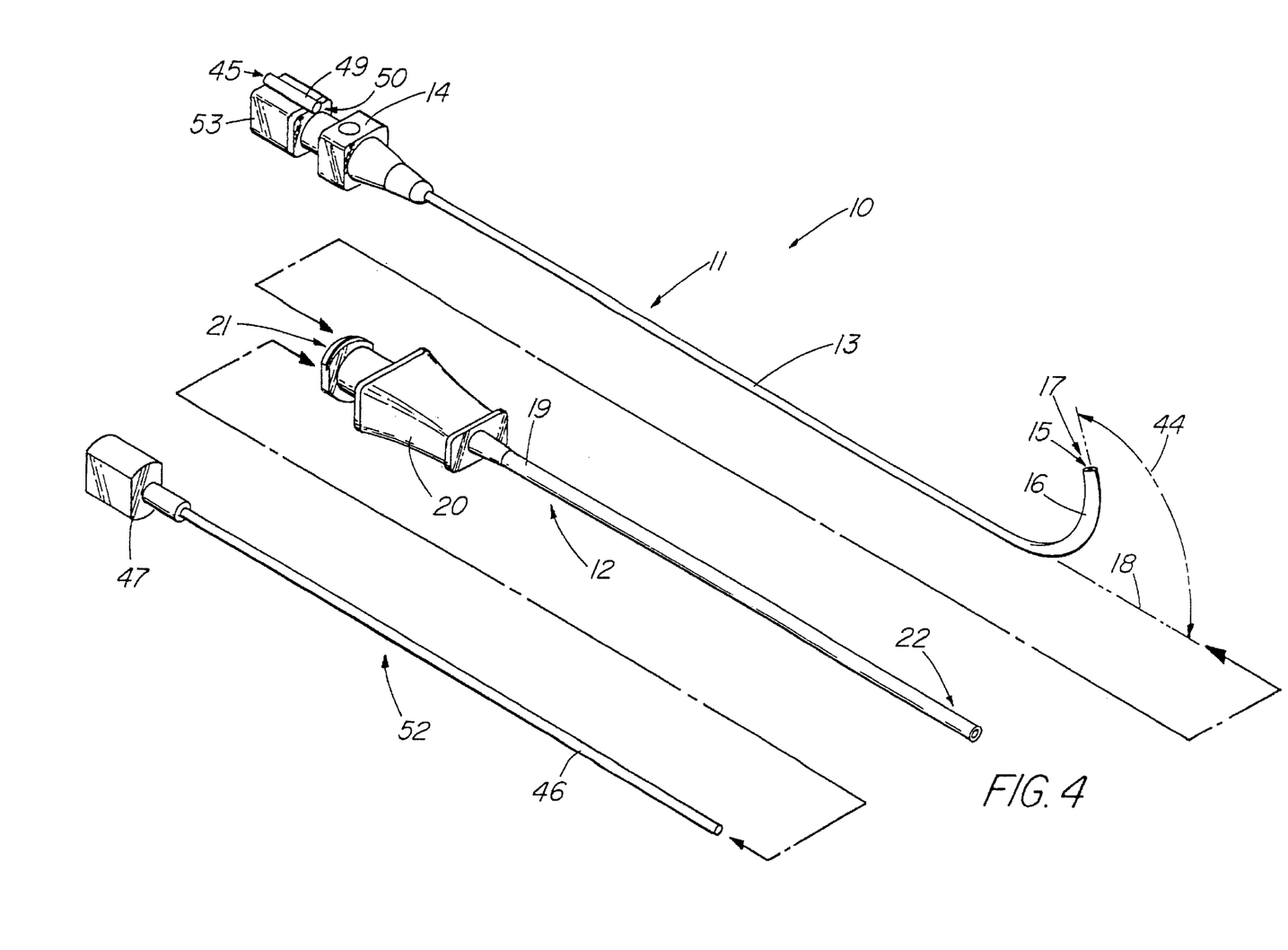
FIG. 4 depicts a pictorial view of a second embodiment of the inner and outer cannula.

FIG. 4 depicts a pictorial view of a second embodiment of the inner curved needle and an outer needle that are adapted for use in the injection of medicaments, contrast media, or other non-viscous agents. The needle 11 is comprised of a smaller gauge needle cannula 13, preferably around 25 gauge, mounted to a proximal hub 14. The preformed bend 16 of individual needle cannula 13 has a slightly tighter radius than in the embodiments of FIGS. 1–3. The coaxial outer cannula 12 includes a correspondingly sized needle cannula 19, preferably around 21 gauge, attached to a standard needle hub that is adapted to receive proximal hub 14 of the needle 11. The embodiment of FIG. 4 is used with a plurality of stylets that are inserted within both the inner and outer needles during their respective introduction into the body. The first is an outer cannula introducer stylet 52 that is inserted into the passageway 21 of the coaxial outer cannula 12. The coaxial outer cannula 12 and outer cannula introducer stylet 52 are inserted together into the patient. The stylet, which is comprised of a stainless steel stylet wire 46 with an attached standard plastic needle hub 47, prevents the coaxial outer cannula 12 from coring tissue into the passageway 21 at the distal tip 22. Once the coaxial outer cannula 12 is in position, outer cannula introducer stylet 52 is withdrawn from the coaxial outer cannula 12 and the needle 11 and second introducer stylet 45 are together inserted into outer needle passageway 21. The inner needle introducer stylet 45, which is longer than outer cannula introducer stylet 52 in order to fit the longer needle 11, serves a similar function to the outer cannula introducer stylet 52 by preventing coring of tissue when the needle 11 is deployed from the coaxial outer cannula 12.

Figure 5:
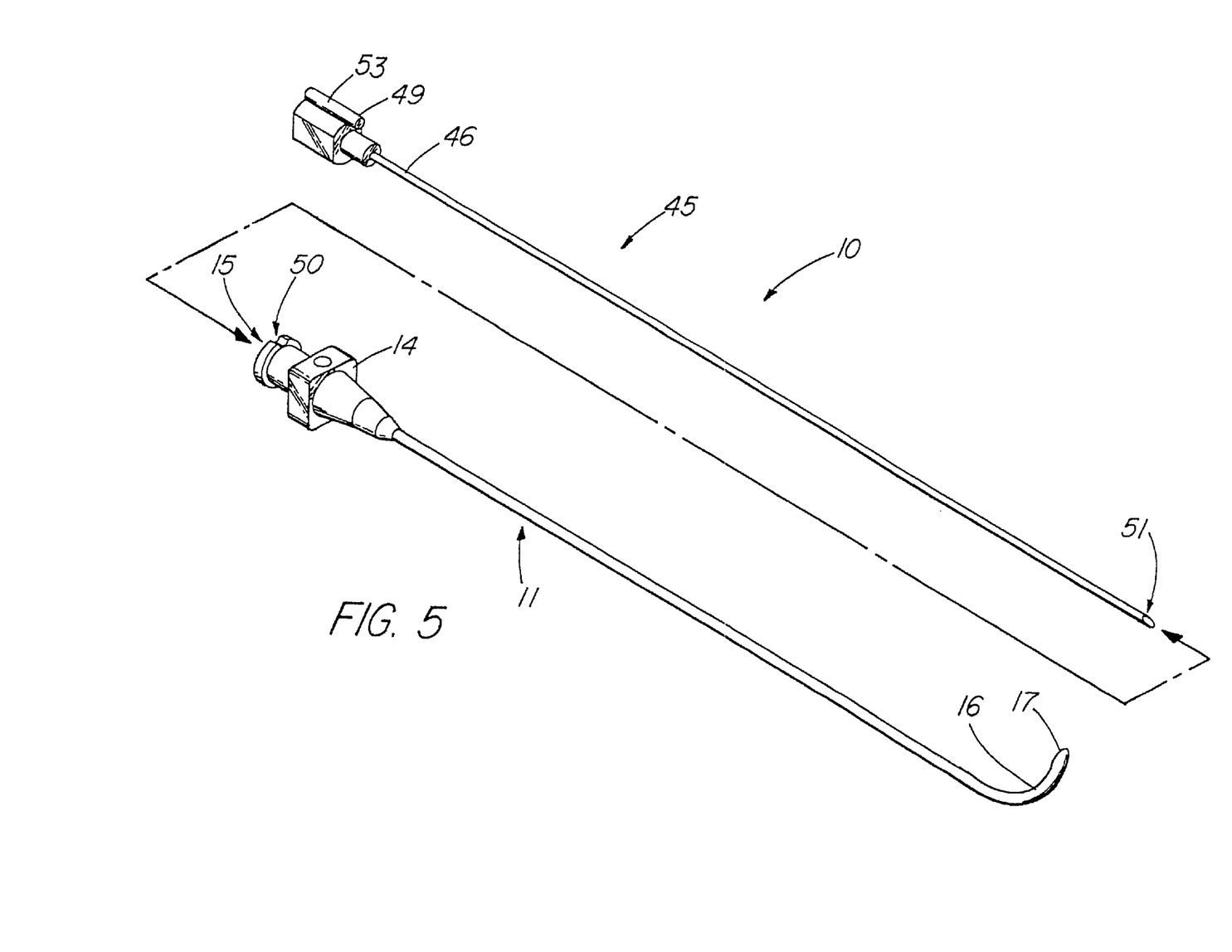
FIG. 5 depicts a pictorial view of the inner cannula of FIG. 4 with an introducer stylet.

As shown in both FIGS. 4 and 5, the proximal hub 14 of the needle 11 is adapted such that the hub 53 of the inner needle introducer stylet 45 locks together with proximal hub 14 to keep the two in alignment. This locking mechanism includes a molded protuberance 49 on hub 53 that fits within a recess 50 on proximal hub 14. The purpose of maintaining alignment of hub 53 and proximal hub 14 is to match the beveled surface 51 at the tip of the inner needle introducer stylet 45, shown in FIG. 5, with the beveled edge at the tip 17 of the needle 11.

Figure 6:
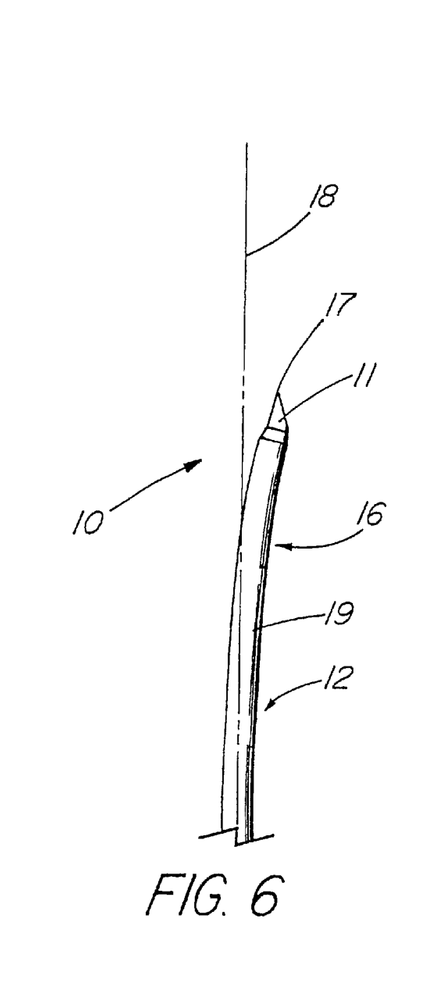
FIGS. 6–8 depict side views of the inner cannula of FIG. 4 being deployed from the outer cannula.
Figure 7:
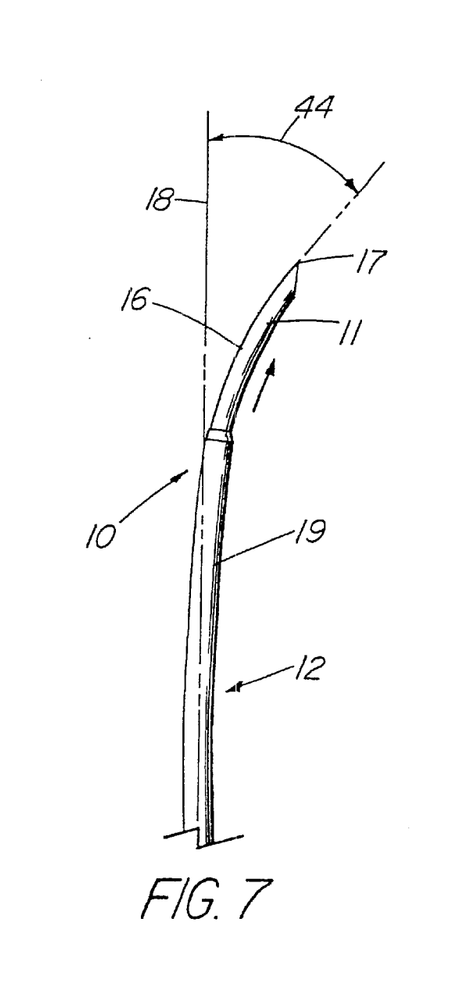
Figure 8:
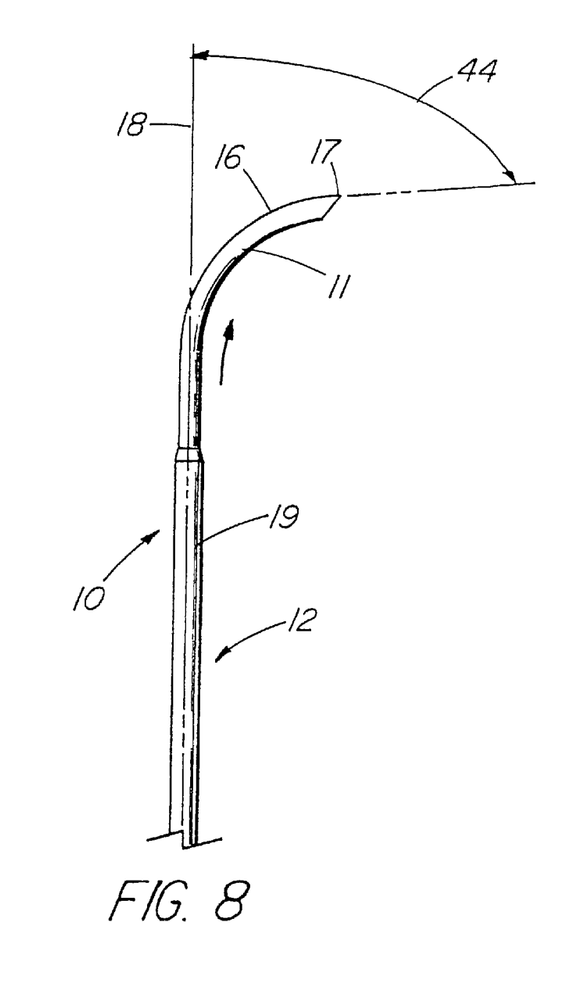

FIGS. 6–8 depict the deployment of the needle 11 from the outer needle cannula 12. FIG. 6 depicts the needle 11 during the initial stage of deployment from the coaxial outer cannula 12. The preformed bend 16 of the needle 11 is constrained by the cannula 19; however, as in the case of the embodiment of FIG. 6, the preformed bend 16 may be of sufficient stiffness to slightly deform the outer cannula 19 while the needle 11 is inside the coaxial outer cannula 12. Despite this slight deformation, the coaxial outer cannula 12 is still substantially straight, as defined herein. As depicted in FIG. 7, the stress that the preformed bend 16 places on the outer cannula 19 is relaxed as the needle 11 is further deployed; and the angle of deflection 44 (as measured from the longitudinal axis 18 of the coaxial outer cannula 12 to the opening at tip 17 of the needle 11) is increased. As the needle 11 is further deployed as depicted in FIG. 8, fully exposing the preformed bend 16 to produce the largest possible angle of deflection 44, the unstressed outer cannula returns to a straight configuration. The phenomenon depicted in FIGS. 6 to 8 is most noticeable when using smaller gauge cannulae as in the embodiment of FIGS. 4 to 5. The larger gauge outer cannula of FIGS. 1 to 3 is more resistant to deformation than that of the second embodiment. Naturally, the tendency of the stressed outer cannula to deform is also very much dependent on the stiffness and radius of the preformed bend 16 as well as the thickness of the cannula wall and material used. To eliminate this deformation during introduction of the device, a stylet 45, as depicted in FIG. 5 can be used as a stiffener until removed immediately before the preformed bend 16 is deployed.

Figures 9, 10, 11:
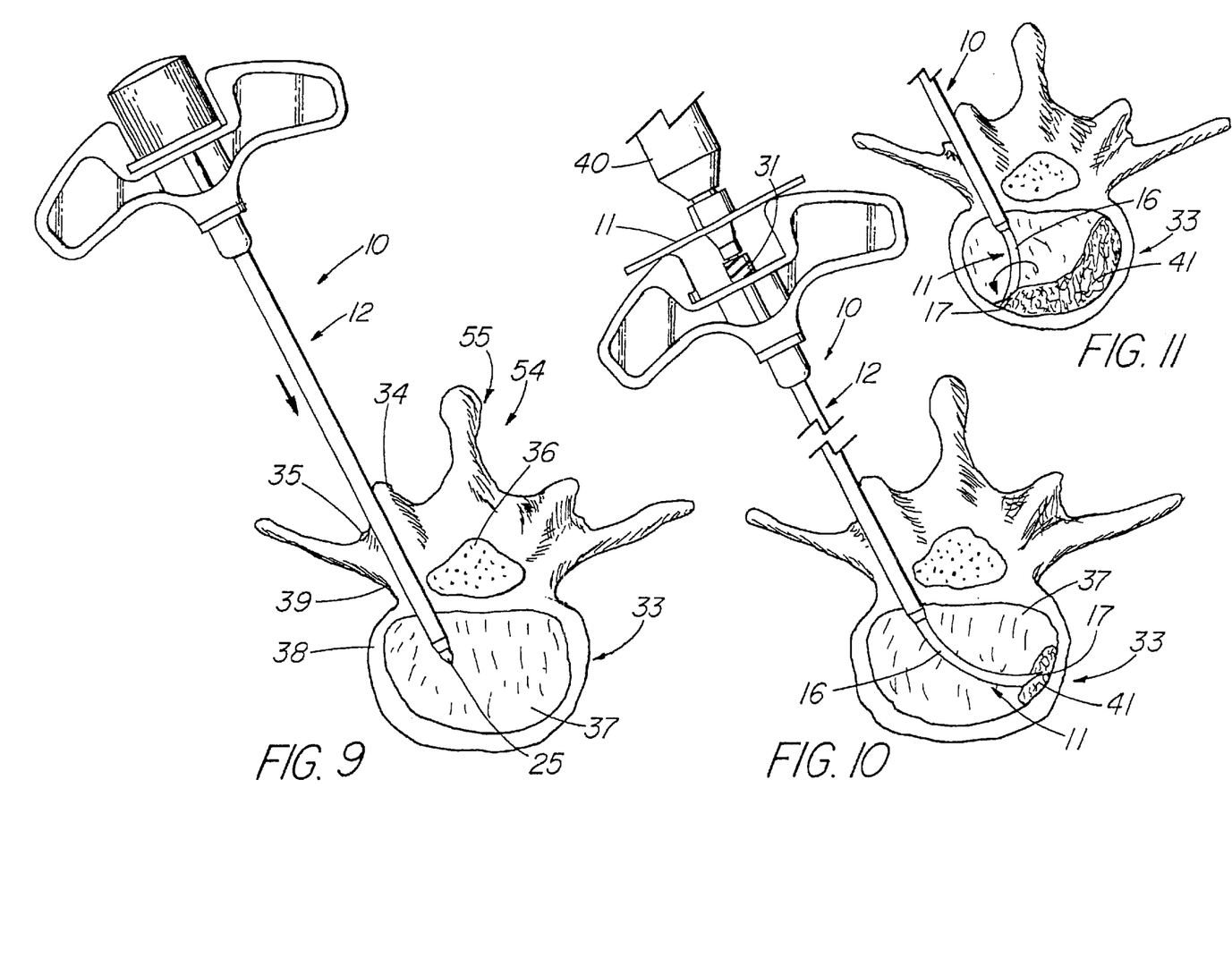
FIG. 9 depicts a partially sectioned view of the apparatus of FIG. 2 being introduced into a vertebral body.
FIGS. 10–11 depict partially sectioned views of the apparatus of FIG. 2 infusing cement into a vertebral body.

FIGS. 9 to 11 depict the use of the present invention to perform a vertebroplasty procedure on a pathological vertebral body 33, using a transpedicular approach. As depicted in FIG. 9, the coaxial outer cannula 12 with introducer trocar 25 is introduced through the wall 38 and into the marrow 37 of the vertebral body 33. The transpedicular route of access places the needle between the mammillary process 34 and accessory process 35 of the vertebral arch 55. The vertebral arch 55 is attached posteriorly to the vertebral body 33 and together, they comprise the vertebra 54 and form the walls of the vertebral foramen 36.

Once the coaxial outer cannula 12 and inner introducer trocar 25 are within the internal region or marrow 37 of the vertebral body, the trocar 25 is withdrawn from the coaxial outer cannula 12 and the infusion needle 11 is inserted in its place. FIG. 10 depicts the infusion needle 11 infusing bone cement 41, commonly methyl methacrylate, into the vertebral body 33 to provide it with improved structural integrity. As depicted in FIG. 11 the infusion needle 11 can be partially withdrawn or rotated to obtain a more complete filling or avoid the network of vertebral veins. Even though the vertebral body may not need to be completely filled, the density of the marrow 37 would still necessitate a second transpedicular stick (when using a conventional straight infusion needle) without the ability of the present invention to infuse cement within multiple planes within the vertebral body 33. At the completion of the procedure, the infusion needle 11 is withdrawn back into the coaxial outer cannula 12 and both are removed from the vertebral body 33.

The utility of the present invention is certainly not limited to procedure involving the spine. The device could be useful in many sites within the body that might require straight access by a needle, followed by indirect or lateral infusion, aspiration, or sampling. For example, the inner needle could be adapted to take biopsy samples from dense tissue, such as a breast lesion, especially where indirect access is might be desirable.

Figure 12:
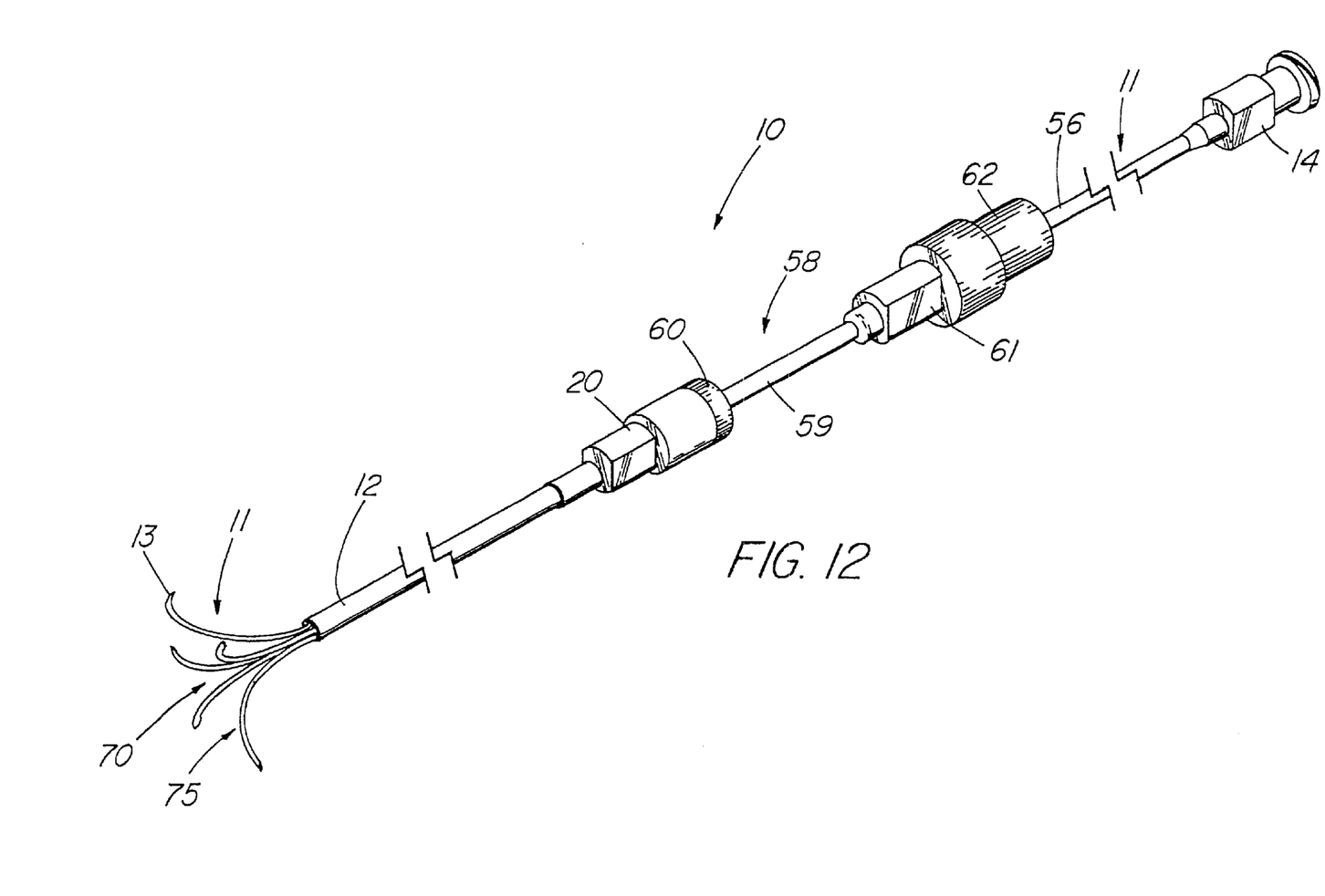
FIG. 12 depicts an isometric view of a third embodiment of the present invention.

With regard to another embodiment of the invention, FIG. 12 depicts a perspective view of the present invention in which the needle assembly 10 comprises a multiple needle assembly 70 useful in infusion of ethanol or other medicaments into a tumor. The needle assembly 10 comprises a needle 11, which in this embodiment includes a multiple needle assembly 70 comprising a plurality of needle cannulae 13, each having a preformed bend 16; a proximal assembly 58 for constraining the multiple needle assembly 70, and a coaxial outer cannula 12 for introducing the multiple needle assembly 70 to its anatomical target. The multiple needle assembly 70, shown in FIG. 13, includes a base cannula 56 affixed to a proximal hub 14 such as a standard female luer fitting. A plurality of needle cannulae 13 are manifolded into the base cannula 56, where their distal tip portions diverge into an array evenly spaced in an umbrella configuration 75, and affixed in place with a solder joint 57. In the illustrative embodiment, five needle cannulae 13 are used, although two to as many as appropriate for the given cannula size can be used. As with the other embodiments, the needle cannulae 13 are preferably made of nitinol that is either annealed or cold-worked to produce the preformed bend 16. In the illustrative embodiment, the coaxial outer cannula 12 has an O.D. of approximately 0.072" and an I.D. of around 0.06", while the individual curved needle cannulae 13 have an O.D. of 0.02" and I.D. of about 0.12". As shown in FIG. 14, the tips 17 of the needle cannulae 13 may be beveled to better penetrate tissue.

Deployment of the curved needle cannulae 13 of the multiple needle assembly 70 is depicted in FIG. 14. The needle cannulae 13 are restrained by the coaxial outer cannula 12 until the multiple needle assembly 70 is advanced, exposing the distal end portions of needle cannulae 13 at distal end 22 of coaxial outer cannula 12, whereby they radiate outward to assume, when fully advanced, the umbrella configuration 75 of FIG. 13.

Figure 13:
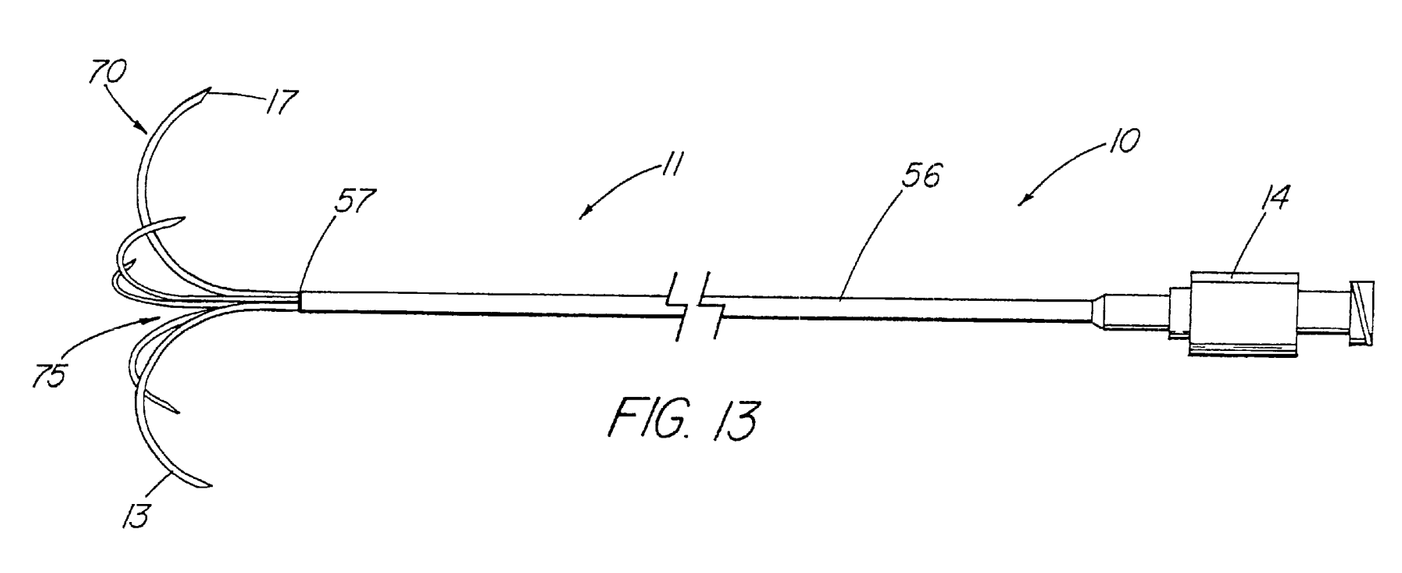
FIG. 13 depicts a side view of the multi-directional infusion needle of FIG. 12.
Figure 14:
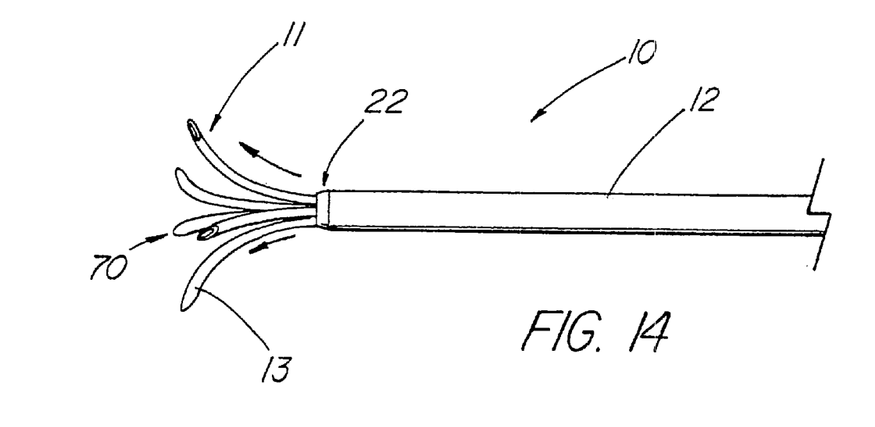
FIG. 14 depicts a side view of the needle of FIG. 13 being partially deployed.
Figure 15:
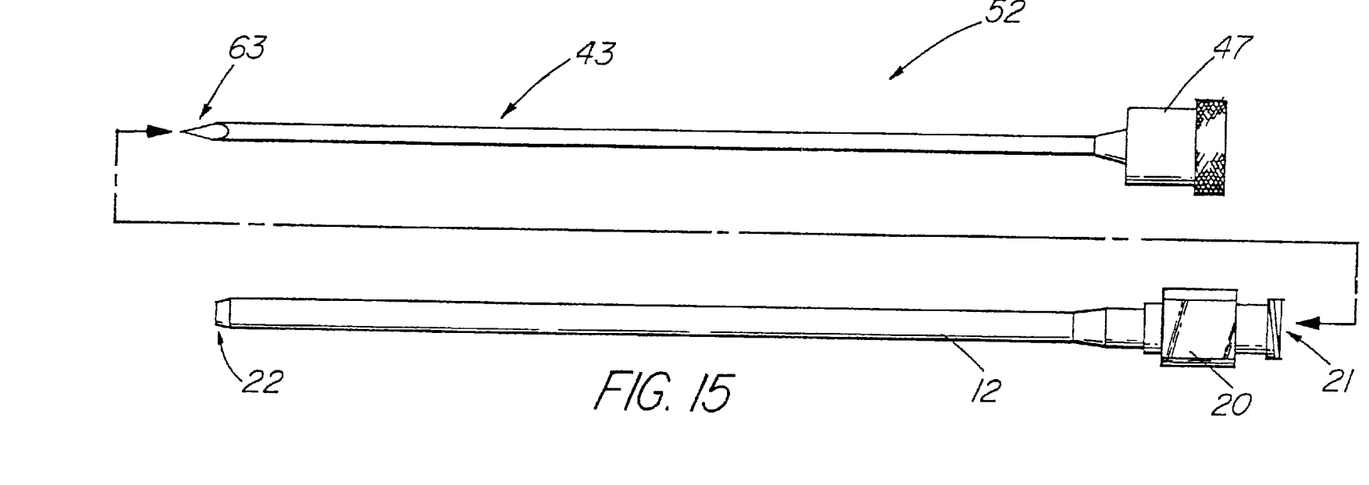
FIG. 15 depicts a side view of the trocar introducer used with the embodiment of FIG. 12.

FIG. 15 depicts a side view of an outer needle assembly comprising a coaxial outer cannula 12 and outer cannula introducer stylet 52 used in placement of the multiple needle assembly 70 of FIGS. 12–14. The outer cannula introducer stylet 52 is inserted into passageway 21 of coaxial outer cannula 12 with the male proximal hub 47 of the outer cannula introducer stylet 52 fitting into the female proximal hub 20 of the coaxial outer cannula 12 when the outer cannula introducer stylet 52 is fully advanced. The outer cannula introducer stylet 52 includes a sharp tip 63, such as the diamond-shape tip depicted, for penetrating tissue. In the present embodiment, the outer cannula introducer stylet 52 and coaxial outer cannula 12 are introduced percutaneously into the liver or kidney and placed at the desired treatment location. The outer cannula introducer stylet 52 is then removed. The proximal assembly 58 with the preloaded multiple needle assembly is then advanced into the coaxial outer cannula 12 which remains in the patient. In the illustrative embodiment, the coaxial outer cannula has an O.D. of 0.095" and I.D. of about 0.076", while the O.D. of the inner stylet is about 0.068".

Figure 16:
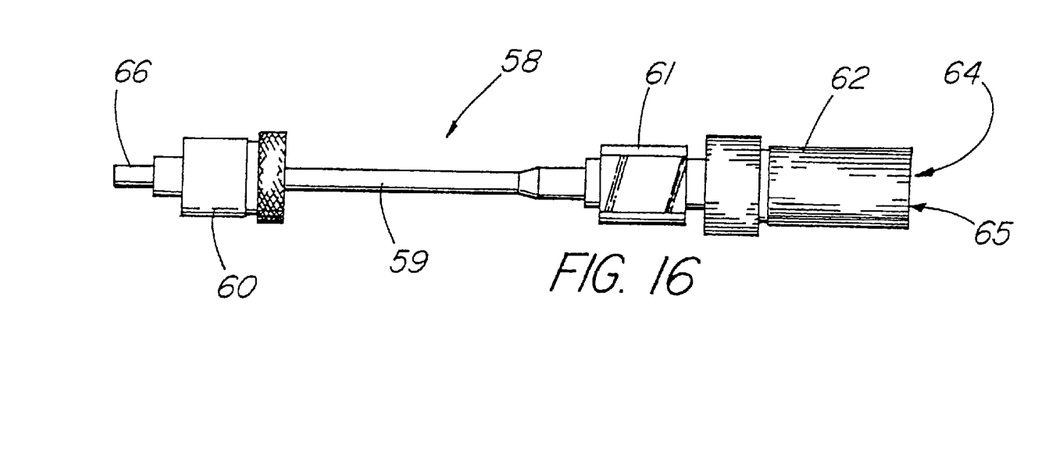
FIG. 16 depicts a side view of the proximal assembly of FIG. 12.

FIG. 16 depicts a side view of the proximal assembly 58 of FIG. 12. The proximal assembly 58 includes a distal male adaptor 60 connected to an intermediate cannula 59 that is sufficiently large to accommodate the multiple needle assembly 70. At the proximal end of the intermediate cannula 59 is proximal assembly female adaptor 61 which is connected proximally to a proximal assembly hub 62, such as a Tuohy-Borst adaptor. The proximal assembly hub 62 is utilized by the physician during manipulation of the device. The multiple needle assembly 70 of FIG. 13 is loaded into lumen 64 at the proximal end 65 of the proximal assembly hub 62, the needle cannulae 13 remaining within the intermediate cannula 59. The distal end 66 of the proximal assembly 58 with the preloaded multiple needle assembly 70 is then inserted into the proximal hub 20 of the coaxial outer cannula as depicted in FIG. 12. The multiple needle assembly 70 is then advanced from the proximal assembly 58 into the coaxial outer cannula 12 where it is deployed as depicted in FIGS. 12 to 14. Ethanol is infused into the multiple needle assembly 70 via the proximal hub 14 of the infusion needle 11. Following treatment, the multiple needle assembly 70 is withdrawn into the coaxial outer cannula 12 and the entire needle assembly 10 is removed from the patient.

Figures 21, 22:
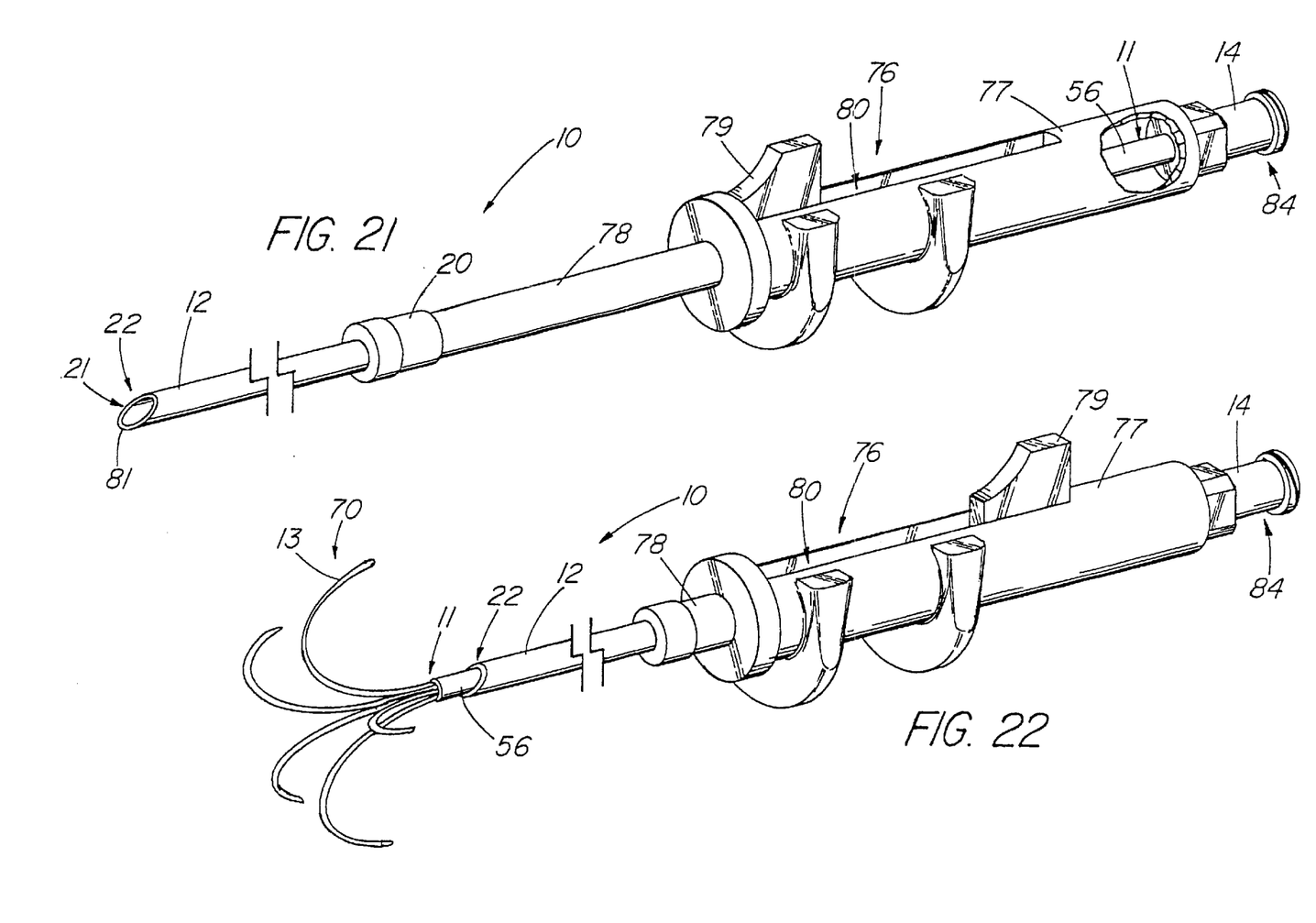
FIGS. 21–22 depict pictorial views of a fifth embodiment of the present invention.

FIGS. 21–22 depict a variation of the needle assembly 10 of FIG. 12 in which the needle 11 and the coaxial outer cannula 12 are connected to a coaxial handle 76 used to advance and deploy the multiple needle assembly 70 from the constraints of the coaxial outer cannula 12. In the illustrative embodiment, the coaxial handle 76 comprises a stationary outer component 77 that fits over the base cannula 56 of the multiple needle assembly 70 and attaches to proximal hub 14; and a slidable inner component 78 that attaches proximally to proximal hub 20. The slidable inner component 78 further comprises a thumb piece 79 used by the physician to advance or retract the coaxial outer cannula 12 as the slidable inner component 78 retracts into the stationary outer component 77. In FIG. 21, the needle assembly is depicted in the introducer position with he thumb piece 79 advanced fully forward within the slot 80 in the outer slidable component 77. FIG. 22 depicts the deployment state of the needle assembly 10 in which the thumb piece 79 has been moved to the most proximal position within the slot 80. In this position, the coaxial outer cannula 12 is retracted to fully expose the plurality of needle cannulae 13 which can assume their unconstrained configuration that includes the preformed bends 16. It should be noted that this type of handle can be used with both the multiple and single infusion needle where a introducer trocar or stylet is not required. Other well-known types of coaxial handles 76 include, but are not limited to, screw-type, rachet-type, or trigger-activated handles which allows the coaxial outer cannula 12 to be longitudinally displaced relative to the needle 11. To reduce the needle for a trocar or stylet for facilitating the penetration of tissue, the distal tip 22 of the coaxial outer cannula 12 can be shaped into a needle point such as depicted, or a non-coring point to help maintain an open outer cannula passageway 21. As with each of the embodiments, a syringe or other reservoir container can be attached to proximal hub 14 as an infusate source or for collection of aspirated material. In addition, the reservoir, such as a syringe, can be incorporated internally within the coaxial handle 76 of the needle assembly 10, or integrally attached thereto.

Figure 17:
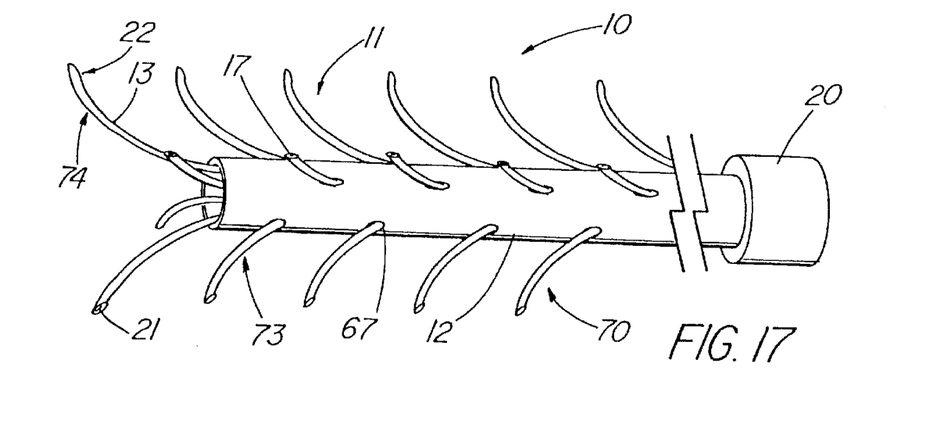
FIG. 17 depicts a side view of a fourth embodiment of the present invention.

Another embodiment of the multiple needle assembly 70 is depicted in FIGS. 17–20 whereby there are one or more groupings of proximally-located needles 73 in addition to the distally-located needles 74 that are similar to the embodiment of FIG. 12. By locating needle cannulae 13 proximal to those at the distal end such that their distal tips are staggered axially upon deployment wider dispersal and coverage is attained for infusion of medicaments. In the embodiment of FIG. 17, there is an arrangement of four needle cannulae comprising the distally-located needles 74, while at least one other group comprising proximally-located needles 73 located along the length of the needle 11 provides simultaneous infusion in a more proximal location. The needle cannulae 13 of the proximally-located and distally-located needles 73,74 can vary in their configuration, length, number, and how they are attached to the base cannula 56 (FIG. 13). For example, individual needle cannulae 13 within an umbrella configuration 75 or between proximally-located and distally-located needles 73,74 can be longer, or have a different radius than others to vary the distribution pattern of the infusate. In one embodiment depicted in FIGS. 17–18, each pair of oppositely-disposed needle cannulae 13 within a grouping of four proximally-located needles 73 are longitudinally offset with respect to the adjacent pair located 90° therefrom, as are the side apertures 67 from which they emerge. With regard to attachment, possibilities include, but are not limited to, having all needle cannulae 13 attaching to a single base cannula 56; dividing the base cannula 56 such that a separate portion extends distally from the proximally-located needles 73 to join the distally-located needles 74; or elimination of the base cannula 56 such that the needle cannulae 13 of the multiple needle assembly 70 are separate and run the length of the needle 11.

Figure 18:
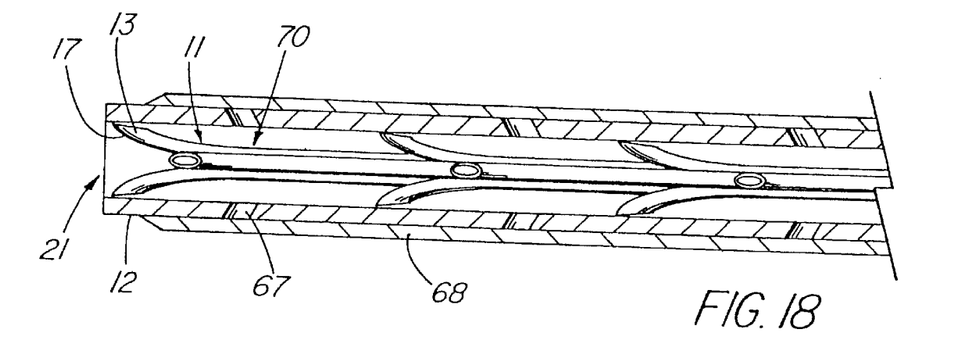
FIG. 18 depicts a partially-sectioned side view of the embodiment of FIG. 17 prior to deployment.
Figure 19:
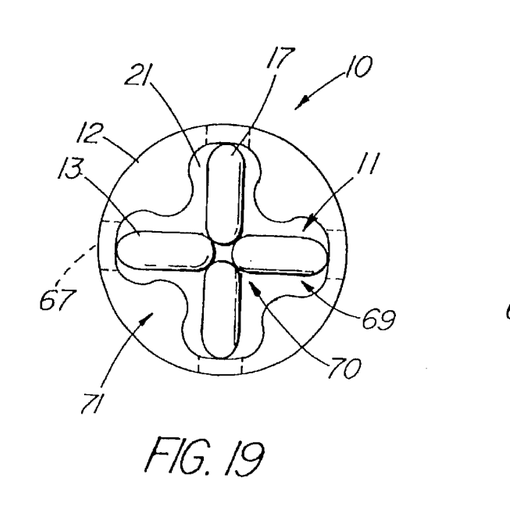
FIGS. 19–20 depict cross-sectional views of two embodiments of coaxial outer cannula depicted in FIG. 17.
Figure 20:
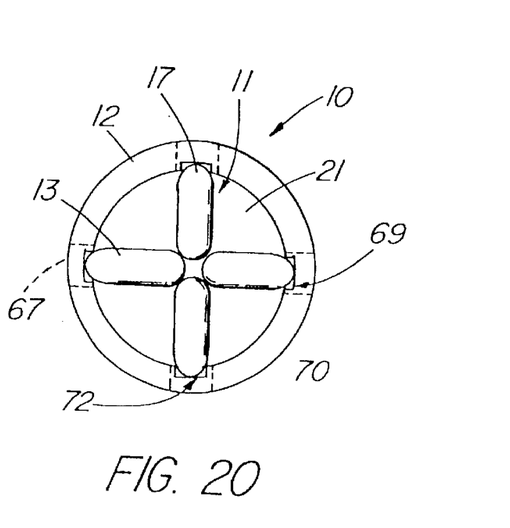

To constrain the needle cannulae 13 for introduction along a single pathway into the body, a coaxial outer cannula 12 is used that has side apertures 67 in the cannula to permit the proximally-located needles 73 to deploy outward therethrough for lateral infusion. FIG. 18 shows a sectioned view of the needle assembly of FIG. 17 in which the needle cannulae 13 are constrained in the introduction position. An introducer cannula 68 is used to selectively expose the side apertures 67 in embodiments where the arrangement of needles is such that individual needle cannulae 13 may prematurely exit a non-designated hole or row, preventing or delaying proper deployment of the multiple needle assembly 70. By maintaining the introducer sheath over the side apertures 67 until the distally-located needles 73 are deployed, proper deployment of all needle cannulae 13 is easier to attain. FIGS. 19–20 illustrate intraluminal guides 69 to help facilitate proper alignment of needle cannulae 13 with a designated side aperture 67. In FIG. 19, a series of ridges 71 within the passageway 21 of the coaxial outer cannula 12 help guide the needle cannulae 13 to align with a designated side aperture 67. FIG. 20 depicts an alternative intraluminal guide 69 in which the needle cannulae 13 travel longitudinally within grooves 72 that are made in the inside wall of the passageway 21.

It is thus seen that the present invention has utility in a variety of medical procedures, and variations and modifications of the curved needle of the present invention additional to the embodiments described herein are within the spirit of the invention and the scope of the claims.

What is claimed is:

1. A needle assembly comprising:
   an infusion needle having a plurality of needle cannulae each having a distal tip, the plurality of needle cannulae, while in their unconstrained configuration, each having a preformed bend proximate to a respective said distal tip with an angle within a range from 40 to 90°, the preformed bends further comprising mechanically-induced martensite with straight portions of said inner hollow cannula comprised of austenitic state Ni—Ti alloy, the plurality of needle cannulae constrainable to a second configuration that is substantially straight, whereby at release of external constraining forces, the plurality of needle cannulae substantially return to their unconstrained configurations, the needle cannulae comprising a Ni—Ti alloy, the preformed bends of the plurality of needle cannulae induced by mechanically deforming the needle cannulae, each preformed bend includes a martensitic crystalline structure, while non-mechanically deformed portions of the needle cannulae comprise a substantially austenitic crystalline structure;
   a coaxial outer cannula having a distal end and a passageway therethrough, the needle cannulae adapted to be disposed inside the passageway of the coaxial outer cannula to constrain the needle cannulae into the second configuration; the needle cannulae being slidably deployable from the distal end of coaxial outer cannula whereby at release of constraining forces from said distal tips and said preformed bends, the plurality of needle cannulae substantially return to their unconstrained configurations with respective said distal tips thereof extending in respective directions forwardly and radially outwardly from respective said preformed bends;

an inner needle introducer stylet having a stylet shaft, the stylet shaft being insertable into the passageway of the infusion needle; and an outer cannula introducer stylet that is insertable into the passageway of the coaxial outer needle such that the coaxial outer needle and outer cannula introducer stylet comprise an outer needle assembly adapted for insertion into the body of a patient.

2. A needle assembly comprising:

a plurality of needle cannulae each having a passageway and a distal tip portion, each said needle cannula, while in its unconstrained configuration, having at least one preformed bend proximate to said distal tip portion and being constrainable to a second configuration, whereby at release of external constraining forces, said distal tip portion of each said needle cannula substantially returns to the unconstrained configuration extending forwardly and radially outwardly from a respective said preformed bend.

3. The needle assembly of claim 2 wherein the plurality of needle cannulae radiate outward from a proximal cannula forming a multiple needle assembly.

4. The needle assembly of claim 3 wherein the distal tip portions radiate outwardly in diverging directions defining an umbrella array.

5. The needle assembly of claim 2 wherein the multiple needle assembly includes both at least one proximally-located needle cannula and at least one distally-located needle cannula.

6. The needle assembly of claim 5 further including a coaxial outer cannula for constraining the needle cannulae into the second configuration, the outer cannula having one or more side apertures for deployment of at least one of the proximally-located needle cannulae outwardly therethrough.

7. The needle assembly of claim 6 further comprising an introducer cannula to selectively expose the one or more side apertures for deployment outwardly therethrough of a respective said distal tip portion of the at least one proximally-located needle cannula.

8. The needle assembly of claim 6 further comprising intraluminal guides within the coaxial outer cannula to facilitate alignment of needle cannulae with respective side apertures.

9. The needle assembly of claim 6 wherein said needle cannulae are arranged to have respective distal tips thereof in positions that are staggered axially upon deployment from said coaxial outer cannula.

10. The needle assembly of claim 2, wherein the second configuration is substantially straight.

11. The needle assembly of claim 2 wherein at least one of said needle cannulae comprises a superelastic material.

12. The needle assembly of claim 11 wherein the superelastic material includes a Ni—Ti alloy.

13. The needle assembly of claim 11 whereby the at least one preformed bend is induced by mechanical deformation of the needle cannula such that the superelastic material of the at least one preformed bend includes a martensitic crystalline structure, while non-mechanically deformed portions of the needle cannula comprise a substantially austenitic crystalline structure.

14. The needle assembly of claim 2 further comprising an inner needle introducer stylet having a stylet shaft, the stylet shaft being insertable into the passageway of the needle.

15. The needle assembly of claim 14 wherein the stylet shaft comprises a flexible polymeric material.

16. The needle assembly of claim 2 further comprising a member for constraining the needle cannulae in the second configuration.

17. The needle assembly of claim 15 wherein the constraining member coextends along the needle cannulae.

18. The needle assembly of claim 17, further comprising a coaxial outer cannula for constraining the at least one needle cannula into the second configuration.

19. A needle assembly comprising:

a plurality of needle cannulae made of a superelastic material each, while in its unconstrained configuration, having at least one preformed bend; and a coaxial outer cannula having a distal end and a passageway therethrough, the needle cannulae adapted to be disposed within and along the passageway of the coaxial outer cannula for constraint of the needle cannulae in a second configuration; the needle cannulae being slidably deployable from the distal end of coaxial outer cannula whereby at release of constraining forces, the needle cannulae substantially return to their unconstrained configurations.

20. The needle assembly of claim 19 wherein the distal end of the coaxial outer cannula includes a sharpened tip adapted for the penetration of tissue.

21. The needle assembly of claim 19 wherein the superelastic material includes a Ni—Ti alloy.

22. The needle assembly of claim 19 whereby the at least one preformed bend is induced by mechanical deformation of the needle cannulae such that the superelastic material of the at least one preformed bend includes a martensitic crystalline structure, while non-mechanically deformed portions of the needle cannulae comprise a substantially austenitic crystalline structure.

23. A needle assembly comprising:

a plurality of needle cannula each having a distal tip, each of the needle cannulae while in its unconstrained configuration having a preformed bend with an angle within a range from 40 to 90°, the preformed bend further comprising mechanically-induced martensite with straight portions of said needle cannulae comprised of austenitic state Ni—Ti alloy, the needle cannulae constrainable to a second configuration that is substantially straight, whereby at release of external constraining forces, the needle cannulae substantially return to their unconstrained configurations; and a coaxial outer cannula having a distal end and a passageway therethrough, the needle cannulae adapted to be disposed within and along the passageway of the coaxial outer cannula to constrain the needle cannuae into the second configuration; the needle being slidably deployable from the distal end of coaxial outer cannula whereby at exiting from the distal end the needle cannulae substantially return to their unconstrained configurations with respective distal tip portions thereof extending in respective directions forwardly and radially outwardly in diverging directions from respective said preformed bends.

* * * * *